United States Patent
Brugger (12)

(10) Patent No.: US 6,322,551 B1
(45) Date of Patent: Nov. 27, 2001

(54) BREAK-APART TUBING CONNECTORS FOR USE IN DIALYSIS BLOOD TUBING SETS

(75) Inventor: James Brugger, Newburyport, MA (US)

(73) Assignee: Gambro Inc., Lakewood, CO (US)

( * ) Notice: Subject to any disclaimer, the term of this patent is extended or adjusted under 35 U.S.C. 154(b) by 0 days.

(21) Appl. No.: 09/350,824

(22) Filed: Jul. 9, 1999

(51) Int. Cl.[7] .................................................. A61M 25/00
(52) U.S. Cl. ........................................... 604/533; 604/905
(58) Field of Search ..................... 604/264, 523, 604/533, 535, 538, 905, 4.01, 6.16; 138/118, 120, 155

(56) References Cited

U.S. PATENT DOCUMENTS

| | | |
|---|---|---|
| 2,737,951 | 3/1956 | Braun . |
| 3,217,710 | 11/1965 | Beall et al. . |
| 3,342,179 | * 9/1967 | Ellmann . |
| 3,670,727 | 6/1972 | Reiterman . |
| 3,976,311 | 8/1976 | Spendlove . |
| 3,994,412 | 11/1976 | Difiglio . |
| 4,228,835 | * 10/1980 | Robinson et al. . |
| 4,770,787 | 9/1988 | Heath et al. . |
| 5,071,413 | 12/1991 | Utterberg . |
| 5,152,755 | 10/1992 | Yoshinori . |
| 5,221,267 | 6/1993 | Folden . |
| 5,236,417 | * 8/1993 | Wallis . |
| 5,250,041 | 10/1993 | Folden et al. . |
| 5,259,843 | 11/1993 | Watanabe et al. . |
| 5,693,008 | 12/1997 | Brugger et al. . |
| 5,836,619 | 11/1998 | Shemesh et al. . |

FOREIGN PATENT DOCUMENTS

WO 85/02122   5/1985   (WO) .

* cited by examiner

*Primary Examiner*—Anhtuan T. Nguyen
*Assistant Examiner*—LoAn H. Thanh
(74) *Attorney, Agent, or Firm*—Laura M. Butterfield; Edna M. O'Connor; Peter B. Scull

(57) ABSTRACT

A connector for use in a dialysis tubing set in which the venous and arterial tubing connector ends are integrally molded into a one break-apart connector, such that the connector ends may be easily broken apart to form two distinct connector ends. Prior to use in a dialysis procedure, the connector ends are separated into two distinct connector ends by a manual snap breakage of the coupled connector ends at a line of weakness or partially scored portion of the integrally molded break-apart connector. Once separated from each other through manual separation of the connector, each connector end is connected to respective ports on the same medical apparatus. In this invention, the connector ends themselves are preferably each made in the respective color that corresponds to the color of either of the respective ports on the medical device.

18 Claims, 6 Drawing Sheets

BREAK-APART TUBING CONNECTORS FOR USE IN DIALYSIS BLOOD TUBING SETS

FIELD OF THE INVENTION

The present invention relates generally to tubing connectors for use in dialysis blood tubing sets; and more particularly to integrally formed tubing connectors which are broken apart prior to use in dialysis.

BACKGROUND OF THE INVENTION

The present invention improves upon sterile disposable tubing sets used in hemodialysis. Sterile disposable tubing sets are advantageous in dialysis procedures because they need to be sterilized once and are only used once and are then discarded. In hemodialysis, the patient's blood is removed from the patient's body, anticoagulated, and circulated in an extracorporeal tubing circuit through a dialyzer or artificial kidney. This removes toxic substances such as urea and creatinine from the blood. Typically, a complete hemodialysis procedure is repeated every other day. Thus, because hemodialysis is performed so frequently, it is highly desirable to keep the cost of each treatment as low as possible. It is also very important to maintain sterility for patient safety. To achieve both of these ends, disposable blood tubing sets have been developed. Indeed, disposable sets such as those shown in Brugger, et al., U.S. Pat. No. 5,693,008 are preferred, because these tubing sets prevent contamination of the dialysis machine, which in turn prevents contamination of dialysis patients. This enhances safety and keeps the cost of each treatment down.

At the present time extracorporeal disposable dialysis tubing sets comprise one or more cannulae for drawing blood from and returning blood to a patient. The blood tubing set typically includes a plurality of medical tubing segments, bubble traps or drip chambers, pressure monitoring sites, air bubble detection sites, access sites, clamps, peristaltic pump headers and possibly numerous other sorts of accessories. As described further in Heath et al., U.S. Pat. No. 4,770,787, the extracorporeal tubing circuit can include a fluid flow cassette that can be mounted on a dialysis machine. The cassette would then preferably have one or more flexible tubes that extend from a sidewall to form a pump loop.

As mentioned, an extracorporeal blood tubing set includes a plurality of tubing segments, two of which particularly are the venous and arterial dialyzer tubing segments and their associated arterial and venous dialyzer connector ends. The venous dialyzer tubing segment comprises a venous dialyzer connector end which may be or may include a luer lock connector apparatus for connecting the venous dialyzer tubing segment to the dialyzer. The arterial dialyzer connector end is adapted to connect the arterial dialyzer tubing segment to the dialyzer as well. The arterial dialyzer connector end may also be or may include a luer lock type of connector. In conventional practice, both the venous and arterial connector ends are covered with loose-fitting caps preferably color-coded. The primary purpose of such caps is the maintenance of sterility of the tubing set and connector ends before installation onto the dialysis machine. A color-coding system has been used whereby the colors of these loose-fitting caps are matched with corresponding colors of the dialyzer ports to which they must be connected. The color coordination is meant to prevent confusion of the inlet and outlet ports on the dialyzer.

In use however, a disadvantage of loose-fitting caps occurs first when the caps are removed prior to connection to the dialyzer. Manually removing the caps covering the connectors provides a potential for contamination of the connector ends by the human operator of the dialysis machine. During this manual removal, the operator may inadvertently touch the sterile connector end that connects to the dialyzer, rendering that connector end non-sterile.

Furthermore, in conventional practice, the distinct elements forming the connector ends have required that each connector end be manufactured separately. By manufacturing the connector ends as an integrally molded product, the cost of manufacturing the tubing set is decreased.

A breakable tubing coupling apparatus was disclosed in Folden, U.S. Pat. No. 5,221,267 for incorporation into a peritoneal dialysis conduit system. Specifically, the Folden patent describes using the breakable tubing coupling apparatus to remove tubing sections after fluid has passed therethrough. In the Folden apparatus, there is fluid communication through the tubing coupling apparatus before the breakable coupling apparatus is separated from the section of tubing entering the peritoneal cavity. The Folden breakable tubing coupling is used to detach tubing segments from the patient after peritoneal dialysis is completed.

It is toward the need to maintain a sterilizable tubing set, to simplify manufacturing and to prevent confusion in connecting the tubing set to both the dialysis machine and to the patient, that the present invention is directed.

SUMMARY OF THE INVENTION

The present invention is directed toward integrally molding the venous and arterial tubing connector ends into a one break-apart connector, such that the connector ends may be easily broken apart to form two distinct connector ends. This is achieved by a manual snap breakage of the coupled connector ends. In this invention, the connector ends themselves are preferably each made in the respective color that corresponds to the color of either the inlet or the outlet ports. Once separated from each other through manual separation of the connector ends at a line of weakness or partially scored portion of the integrally molded break-apart apparatus, the arterial dialyzer connector end is connected to its respective dialyzer port, and the venous dialyzer connector end is connected to its respective dialyzer port.

The present invention further includes molding the arterial cannula connector end and the venous cannula connector end together using a connector as above. The arterial and venous cannula connector ends are broken apart prior to connection to the respective arterial or venous cannulae which are then connected to a patient.

Accordingly, the present invention relates to providing a disposable tubing set containing integrally molded connector ends that are detachable from each other at a line of weakness or scored portion to be connected to a medical device prior to use.

A method of the present invention involves separating the break-apart connectors along a line of weakness or scored portion and then connecting the broken apart connector ends to a medical device before beginning dialysis.

The present invention further relates to a break-apart connector apparatus, containing connection mechanisms on the connector ends that are each to be separately connected to a medical device after the connector ends are broken apart from each other.

One significant aspect of the present invention is that the integrally molded one-piece break-apart connector apparatus may be broken apart by applying manual finger pressure leveraged in a concentrated fashion directed towards the line of weakness or scored portion of the connector apparatus, thereby separating the connector ends at the scored portion.

Another aspect of the present invention is that the break-apart, color-coordinated connector ends allow for simple installation of the connector ends correctly onto the corresponding sites on the medical device.

Yet another aspect of this invention is that by eliminating the removable loose-fitting caps covering the connector ends of prior devices, the number of additional components in each blood tubing set is reduced from four to two. This reduces manufacturing costs.

Further significant aspects of the present invention will be apparent to one skilled in the art from the following detailed description and claims read in conjunction with the accompanying drawings which are described briefly below.

DETAILED DESCRIPTION OF THE PREFERRED EMBODIMENT

Figure 1:
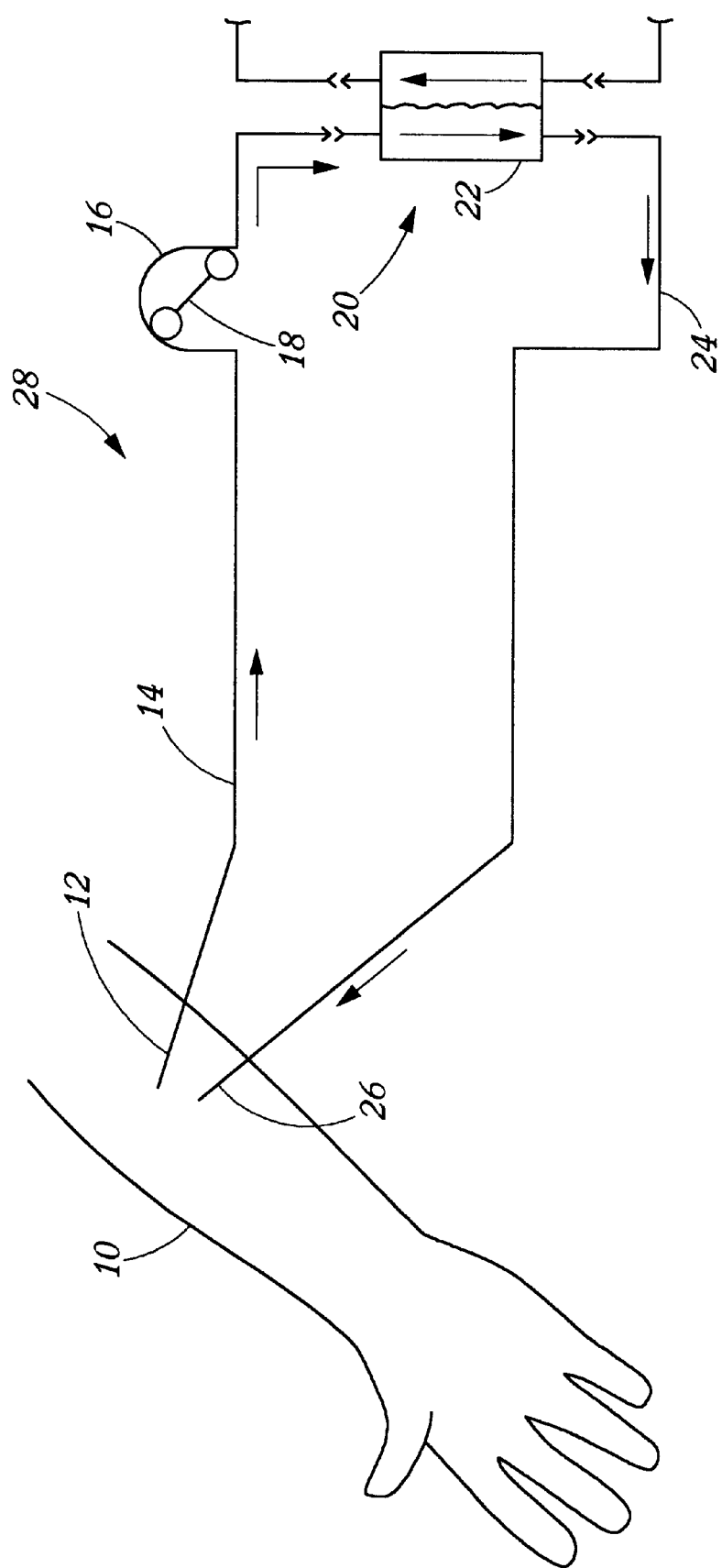
FIG. 1 is a partial schematic diagram illustrating a portion of a typical hemodialysis apparatus and a blood tubing set circuit.

FIG. 1 illustrates schematically a hemodialysis apparatus incorporating a blood tubing set according to the present invention. Blood to be processed or dialyzed, typically referred to as arterial blood because it often is withdrawn from an artery, is withdrawn from a patient 10 through an arterial cannula 12 and flows through an arterial tubing segment 14 of the blood tubing set 28. The arterial tubing segment 14 includes a pump header tubing section 16 which is acted upon by the rotor of a peristaltic pump 18 to move the blood through the tubing lines of the hemodialysis apparatus. The blood then passes into a dialyzer 20. Blood exits the blood chamber 22 of the dialyzer 20 into a venous tubing segment 24 of the blood tubing set and returns to the patient 10 through a venous cannula 26. FIG. 1 is only a schematic or diagramatic illustration representative of a typical hemodialysis circuit. Many variations of this general system are possible which are within the spirit and scope of hemodialysis procedures with which the present invention is forseeably usable.

Figure 2:
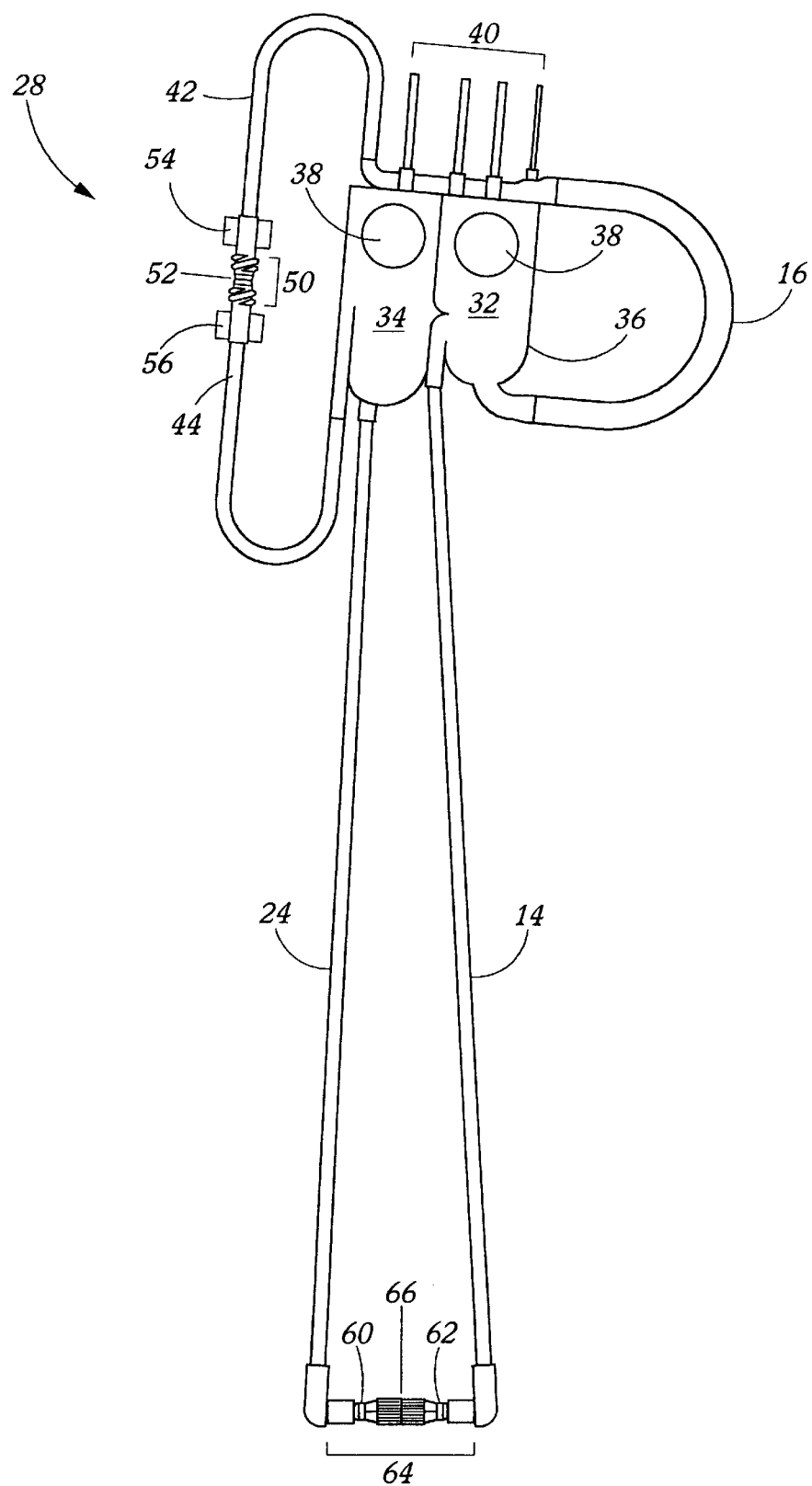
FIG. 2 is an elevational view of a blood tubing set containing break-apart connectors according to the present invention.

As a part of the disposable blood tubing set 28, FIG. 2 shows the connectors of the instant invention before connection to either a dialyzer or cannulae. It should be understood by one skilled in the art that one break-apart connector apparatus or both the dialyzer and cannula break-apart connector apparatuses may be present in a blood tubing set 28 according to the instant invention.

Referring now to the detailed elements of FIG. 2, the blood tubing set 28 includes a fluid flow chamber cassette 36, a blood pump tubing section or loop 16, tubing lines 40 for the addition of heparin, saline, medications or the like, and pressure sensors 38. The fluid flow chamber cassette 36 contains two fluid flow chambers, arterial chamber 32 and venous chamber 34, in which blood accumulates and then out of which blood flows prior to and after passing through a dialyzer (not shown in FIG. 2) through the dialyzer inflow line 42 and dialyzer outflow line 44. As will be described in more detail below, the arterial dialyzer connector end 54 attached to the arterial tubing segment 42 is adapted to connect the arterial tubing segment 42 to the dialyzer (see FIG. 8). The venous dialyzer connector end 56 is similarly adapted to connect the venous tubing segment 44 to the dialyzer (see FIG. 8). The arterial and venous dialyzer connector ends 54, 56 are molded integrally together as a one piece, single connector apparatus 50 before separation and connection to the respective ports on the dialyzer. The dialyzer connector ends 54 and 56 are manufactured with handles 58 to allow for easier gripping and manipulation. The handles 58 are fin-like flat devices protruding out from the body of each dialyzer connector end 54 and 56. The handles 58 provide surfaces for finger contact while gripping and/or twisting to lock each dialyzer connector end into the dialyzer or like receptor. The cassette 36 also contains arterial and venous tubing segments 14 and 24 respectively through which blood is drawn from and returned to the patient as shown in FIG. 1. A preferred cassette 36 is more fully described in U.S. Pat. No. 4,770,787.

The arterial tubing segment 14 and the venous tubing segment 24 are each connectable to a cannula or cannula tubing system (FIG. 8) which takes blood that needs to be dialyzed out of a patient 10 through the arterial tubing segment 14 and returns the dialyzed blood to the patient after completion of the dialysis procedure through the venous tubing segment 24. The arterial cannula connector end 62 is adapted to connect the arterial tubing segment 14 to a fistula needle or cannula 63 (not shown in FIG. 2; but see FIG. 8, below). The venous cannula connector end 60 is adapted to connect the venous tubing segment 24 to a fistula needle or cannula 65 (not shown in FIG. 2) as well. The arterial cannula connector end 62 and venous cannula connector end 60 are molded together in a one piece single connector apparatus 64 before separation and connection to their respective fistula needles.

Break-apart tubing connectors 50 and 64 of the instant invention will now be more fully described with reference to FIGS. 3 through 7.

Figure 3:
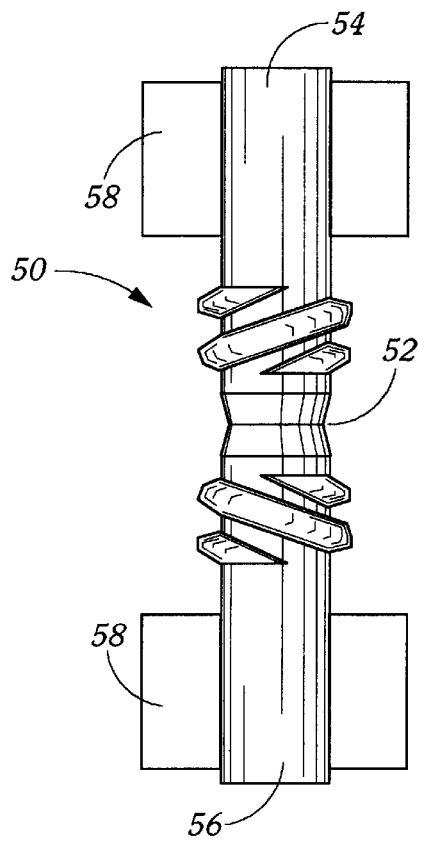
FIG. 3 is an enlarged elevational view of a break-apart arterial-venous dialyzer connector according to the present invention.
Figure 4:
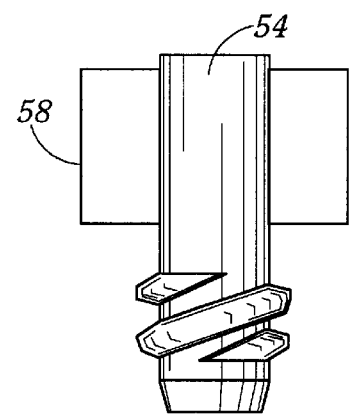
FIG. 4 is an enlarged elevational view of the break-apart arterial-venous dialyzer connector of FIG. 3 after separation into separate connector ends according to the present invention.
Figure 4:
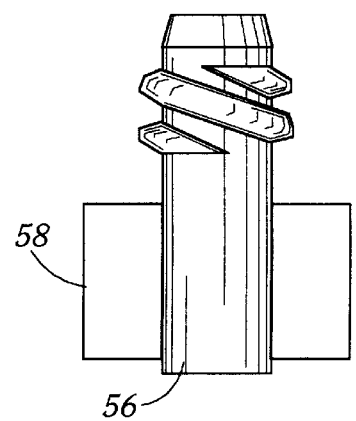

FIG. 3 shows the arterial 54 and venous 56 dialyzer connector ends molded integrally together into one piece 50 before separation. An area or line of weakness 52 is shown around the circumference of the connector. The area or line of weakness may be a scored portion on the connector. It is understood that the scored portion 52 may be partially scored enough to allow separation of the dialyzer connector ends 54 and 56 by grasping each end 54, 56 and applying a bending force (see FIG. 7, for example). It is also understood that the scored portion 52 used to separate the dialyzer connector ends 54 and 56 need not be in the middle of the dialyzer connector ends 54 and 56. The dialyzer connector ends 54 and 56 may be of non-identical sizes. The dialyzer connector ends 54 and 56 are then broken apart prior to attaching them to the dialyzer 20. Broken apart connector ends 54 and 56 are shown in FIG. 4.

Figure 8:
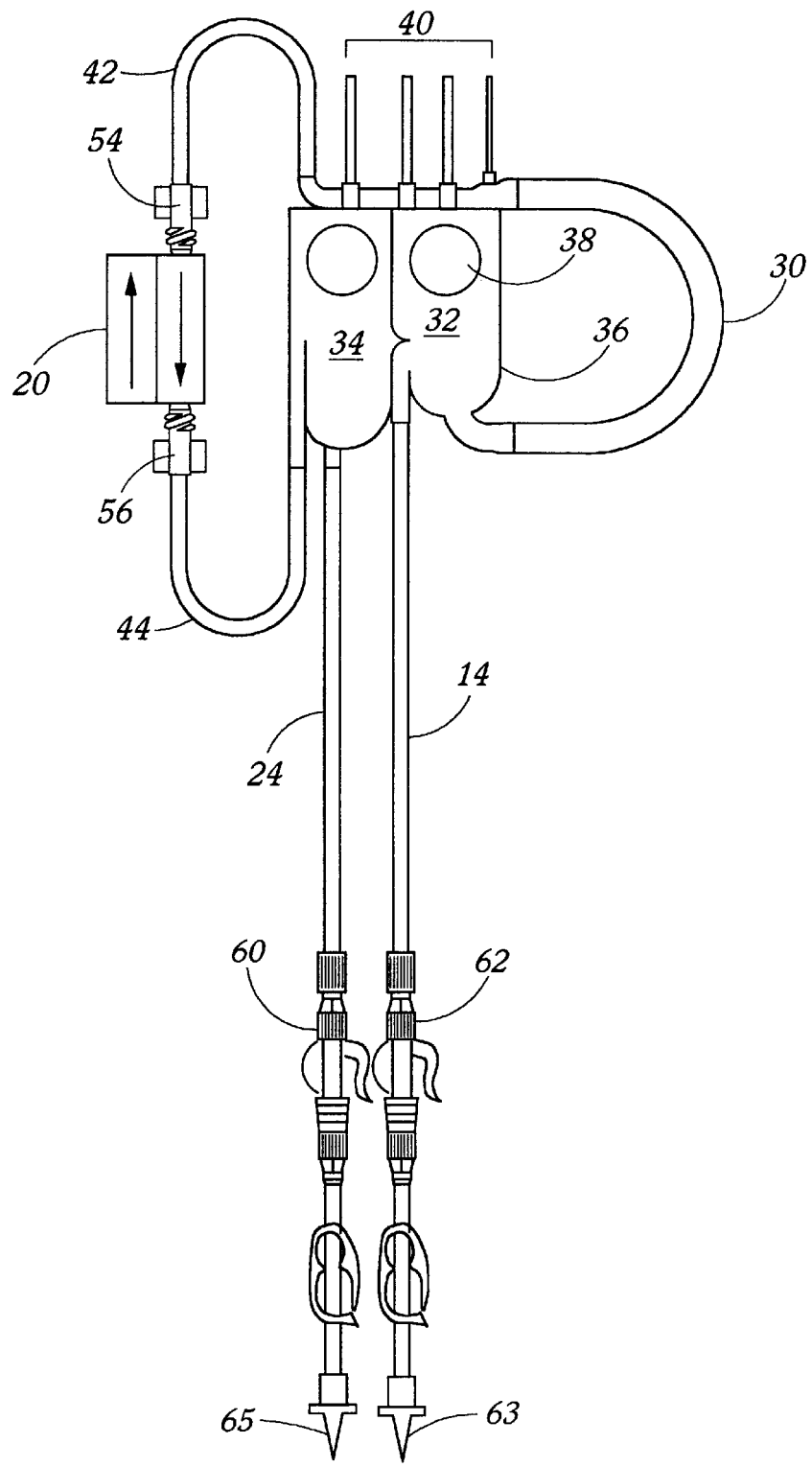
FIG. 8 is an elevation illustrating the dialyzer connector ends connected to both of the dialyzer ports and the respective cannula connector ends connected to the cannulae.

The tubing set 28 is preferably assembled with a connector 50 having the arterial dialyzer connector end 54 being molded integrally with the venous dialyzer connector end 56. The scored portion 52 allows the dialyzer connector ends 54 and 56 to be broken apart easily and attached to the dialyzer (FIGS. 1 and 8). Once attached to the dialyzer 20, the patient's blood can flow from the tubing set 28 through the arterial tubing segment 42 and the arterial dialyzer connector end 54 into the dialyzer to be purified. Purified blood then flows out of the dialyzer 20 through the venous dialyzer connector end 56, through the venous tubing segment 44 and other components of tubing set 28 and ultimately back into the patient 10.

The arterial dialyzer connector end 54 attached to the arterial tubing segment 42 is adapted to connect the arterial tubing segment 42 to the dialyzer 20. The arterial dialyzer connector end 54 may be a luer-lock connector or the like as understood in the art. In the preferred embodiment the dialyzer connector end 54 has a female luer-lock configuration. However, it is also understood that many attachment mechanisms would suffice as well, and that a male luer-lock configuration would also be within the spirit and scope of the invention.

The venous dialyzer connector end 56 is also adapted to connect the venous tubing segment 44 to the dialyzer. The venous dialyzer connector end 56 may also be a luer-lock or the like connector.

The break-apart feature of the dialyzer connector ends 54 and 56 improve upon the prior art by eliminating the loose fitting caps which cover the arterial and venous connector ends and the break-apart feature further helps maintain sterility. The arterial 54 and venous 56 dialyzer connector ends can be molded in different colors to match the often conventional and distinctive colors of the respective inlet and outlet ports of the dialyzer 20. The conventional, separate connector ends have been manufactured with the arterial connectors of a red color, and the venous connectors of a blue color. Molding each dialyzer connector end in the same color that corresponds to the respective connector port on the dialyzer 20 prevents confusion by the dialysis technician as to which dialyzer connector end is intended to be used with and fits into which dialyzer port.

The dialyzer connector ends 54 and 56 of the present invention are preferably molded according to current techniques in the art. Plastic is injected into the mold at locations on the mold that correspond to the side of the connector handles 58. The injected plastic is equally distributed throughout the mold to the connector ends 54, 56 and meets at scored portion 52, preferably forming a weakened weld line. The location of the weld line is controlled through the design of the mold and the molding parameters.

As an alternative manufacturing process, the connector ends 54, 56 may be molded as separate parts and then welded together using RF welding or similar techniques to form a one piece break apart connector 50.

FIG. 4 shows the arterial dialyzer connector end 54 and the venous dialyzer connector end 56 broken apart from each other. The dialyzer connector ends 54 and 56 are broken apart for separate attachments to the opposite sides of the dialyzer 20.

Figure 5:
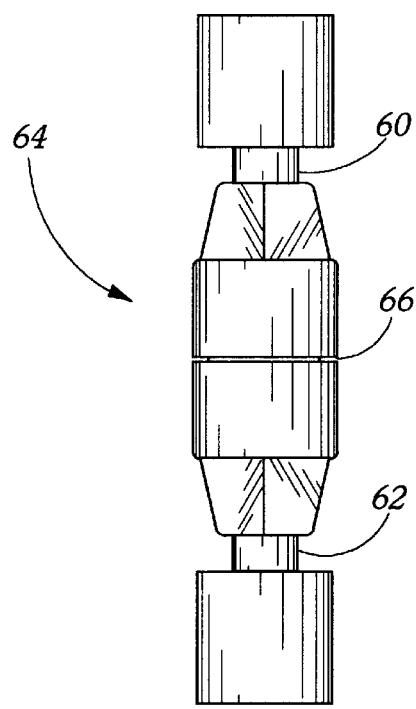
FIG. 5 is an enlarged elevational view of a break-apart arterial-venous cannula connector according to the present invention.
Figure 6:
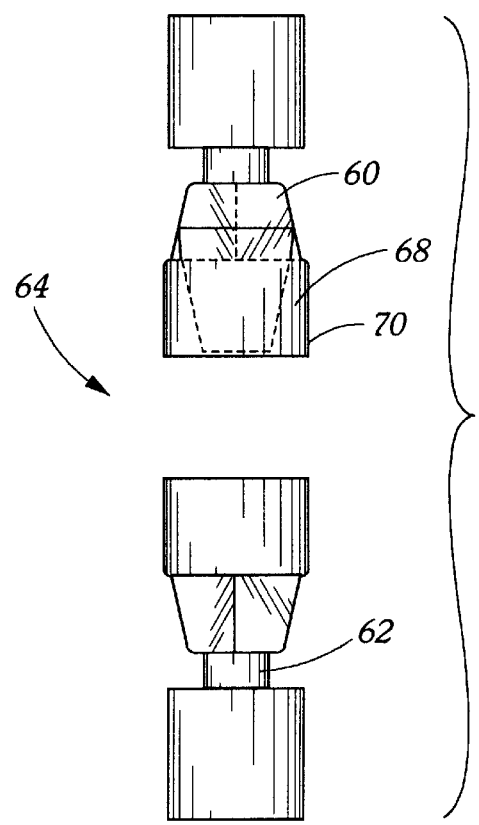
FIG. 6 is an enlarged elevational view of the break-apart arterial-venous cannula of FIG. 5 after separation into separate connector ends according to the present invention.

FIG. 5 shows the arterial cannula connector end 62 and venous cannula connector end 60 molded together in a one piece single connector apparatus 64. The arterial cannula connector end 62 is adapted to connect the arterial tubing line 14 to a fistula needle or cannula 63 (not shown in FIG. 5, but see FIG. 8, below). The connector end may be a luer-lock connector or the like. In the preferred embodiment, the arterial cannula connector end is a male luer-lock. As shown in FIG. 6 as a preferred embodiment, the male luer segment 68 of the connector end is hidden inside the collar 70 of the connector end 60. The venous cannula connector end 60 is also a luer-lock connector. The venous cannula connector 60 is adapted to connect the venous tubing line 24 to a fistula needle or cannula 65 (not shown in FIG. 5, but see FIG. 8) as well.

The arterial and venous cannula connector ends 62 and 60 respectively, are also preferably molded in distinct colors corresponding to the distinct arterial or venous fistula needles 63, 65 (see FIG. 8). The arterial cannula connector end 62 is preferably molded in a red color, and the venous cannula connector end 60 is preferably molded in a blue color. However, it should be easily understood that any number of colors may be used.

The arterial-venous cannula connector 64 is broken apart prior to use. The cannula connector ends 62 and 60 are separated from each other by applying finger pressure to the scored portion 66 (see FIG. 5) of the connector 64. A principle purpose for molding the arterial-venous cannula connector ends together into one piece is to maintain sterility, and prevent contamination of the tubing segments prior to use.

FIG. 6 shows the arterial cannula connector end 62 and the venous cannula connector end 60 broken apart prior to attaching fistula needle luers (not shown in FIG. 6) for insertion into a patient 10.

Figure 7:
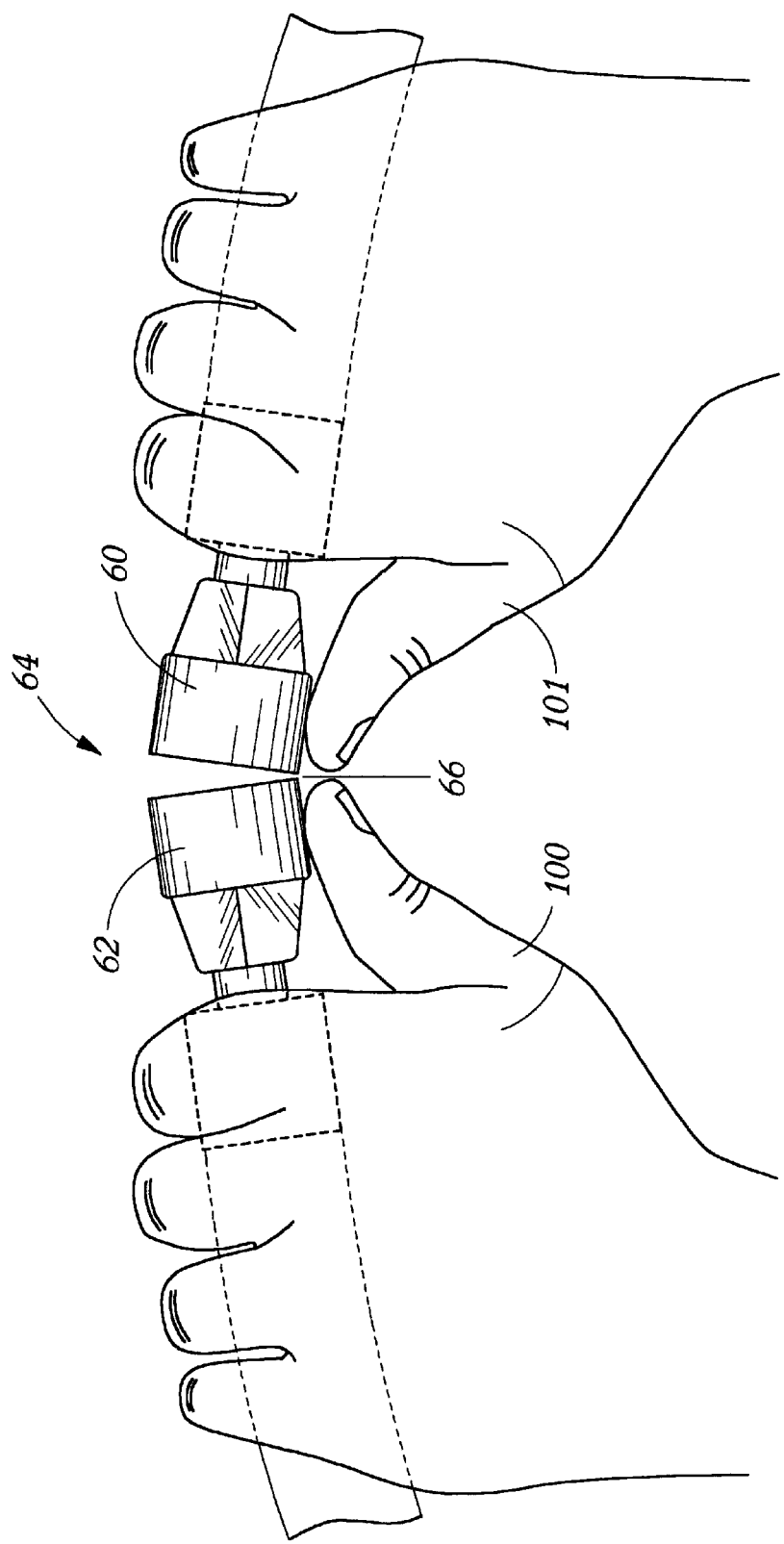
FIG. 7 is an enlarged, not to scale, side view of the break-apart cannula connector apparatus being separated into separate connector ends by the application of finger pressure.

FIG. 7 shows the molded one-piece cannula connector 64 being manually broken apart by the application of finger (or thumb) pressure leveraged in a concentrated fashion at the line of weakness or scored portion 66 of the connector apparatus, separating the arterial cannula connector end 62 from the venous connector end 60 at the scored portion 66. The arterial cannula connector end 54 is separated from the venous cannula connector end 56 (see FIGS. 3 and 4) in a similar fashion. Thumb pressure is shown in FIG. 7 by application of human thumbs 100 and 101.

FIG. 8 shows the arterial dialyzer connector end 54 and the venous dialyzer connector end 56 of the disposable tubing set detached from each other and attached to the dialyzer 20 in preparation for hemodialysis. Once attached to the dialyzer 20, the patient's blood flows through the arterial tubing segment 42 into the dialyzer 20 to be purified. Purified blood flows out of the dialyzer 20 through the venous tubing segment 44 and back to the patient 10.

Also as shown in FIG. 8 in preparation for hemodialysis, the arterial cannula connector end 62 and venous cannula connector end 60 are detached from each other and connected to corresponding fistula needles 63 and 65. The arterial tubing line 14 and venous tubing line 24 are then connected to a patient through use of fistula needles or cannulas 63 and 65. Blood is withdrawn from a patient through an arterial cannula 63 into the arterial tubing segment 14. Dialyzed blood is returned to the patient through a venous tubing segment 24 and venous cannula 65.

A preferred embodiment of the present invention has been described. Many variations of the invention may be made which are within the spirit and scope of the invention as claimed in the following claims.

What is claimed is:

1. A tubing set for connection to a medical device comprising:
   a first tubing segment;
   a second tubing segment;
   and a connector connecting said first tubing segment to said second tubing segment;
   said connector comprising
      a first connector end connected to said first tubing segment;
      a second connector end connected to said second tubing segment;
      whereby said first and second connector ends are connected to each other with a weakened area disposed between the first and second connector ends whereby the weakened area can be broken for disconnection of the first and second connector ends from each other so that each of said first and second connector ends may be connected to a medical device;
      the first connector end and the second connector end further comprising a luer type configuration which are each connectable to a corresponding luer type connection mechanism on a medical device.

2. The tubing set of claim 1 wherein the weakened area comprises a scored portion.

3. The tubing set of claim 2 wherein the scored portion extends partially around the circumference of the connector.

4. The tubing set of claim 1 wherein the connector is a one piece molded apparatus.

5. The tubing set of claim 1 whereby each of said first and second connector ends is color coordinated to correspond to the respective connection mechanism on the medical device.

6. The tubing set of claim 1 wherein the connector is of a plastic material.

7. The tubing set of claim 1 wherein the medical device is a needle or cannula for attachment to a patient.

8. The tubing set of claim 1 wherein said first tubing segment comprises an arterial segment and said second tubing segment comprises a venous segment and wherein said tubing set is comprised of a first arterial connector end and a second venous connector end.

9. The tubing set of claim 1 wherein the medical device is a dialyzer.

10. A breakapart connector for connecting tubing to a medical apparatus, said connector comprising a first connector end connectable to a first tubing segment and a second connector end connectable to a second tubing segment said first and second connector ends being integrally connected to each other and a weakened area between the first and second connector ends whereby the weakened area can be broken for disconnection of the first and second connector ends from each other so that each respective connector end may be connected to a medical apparatus;
   wherein each of the first and second connector ends each comprise a luer type connection configuration which is connectable to a corresponding luer type connection mechanism on the respective medical device.

11. The connector of claim 10 wherein the connector is a one piece molded device.

12. The connector of claim 10 whereby the first and second connector ends are color coordinated to correspond to respective male connectors on a medical device.

13. The connector of claim 10 wherein the connector is of a plastic material.

14. The connector of claim 10 wherein the weakened area comprises the portion between the first and second connector ends that extends at least partially around the circumference of the connector.

15. A method for separating two tubing segments connected to each other by a connector having a weakened area for connection of each tubing segment to a medical apparatus the method comprising;
   breaking the connector into first and second connector ends;
   attaching each connector end on each tubing segment to a respective medical apparatus;
   wherein each connector end has a luer connector configuration and the step of attaching comprises attaching each connector end through the luer connector.

16. The method of claim 15 wherein the step of breaking comprises breaking along the weakened area to control the location of the break.

17. A method for separating two tubing segments connected to each other by a connector having a weakened area for connection of each tubing segment to a medical apparatus the method comprising;
   breaking the connector into first and second connector ends;
   attaching each connector end on each tubing segment to a respective medical apparatus;
   wherein the step of attaching further comprises attaching each connector end to respective parts of a dialyzer.

18. A method for separating two tubing segments connected to each other by a connector having a weakened area for connection of each tubing segment to a medical apparatus the method comprising;
   breaking the connector into first and second connector ends; and
   attaching each connector end on each tubing segment to a respective medical apparatus;
   wherein the step of attaching further comprises attaching each connector end to a needle or cannula for attachment to a patient.

* * * * *